US00PP37806P2

(12) United States Plant Patent
Hartman

(10) Patent No.: US PP37,806 P2
(45) Date of Patent: Oct. 20, 2026

(54) ***CALADIUM* PLANT NAMED 'FCH OF13-807'**

(50) Latin Name: ***Caladium* X *hortulanum***
Varietal Denomination: FCH OF13-807

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 19/639,757

(22) Filed: Apr. 6, 2026

(51) Int. Cl.
*A01H 6/10* (2018.01)
*A01H 5/12* (2018.01)

(52) U.S. Cl.
USPC ..... Plt./373

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Caladium* plant named 'FCH OF13-807', characterized by its upright plant habit and intermediate in height; dense, leafy and bushy appearance; vigorous growth habit and rapid growth rate; large fancy-type leaves that are mostly red in color with dark green and white-colored random blotches, dark green-colored margins and dark green-colored venation; and petioles that are close to black in color with yellow green and white-colored streaks and stripes.

4 Drawing Sheets

Figure 1:
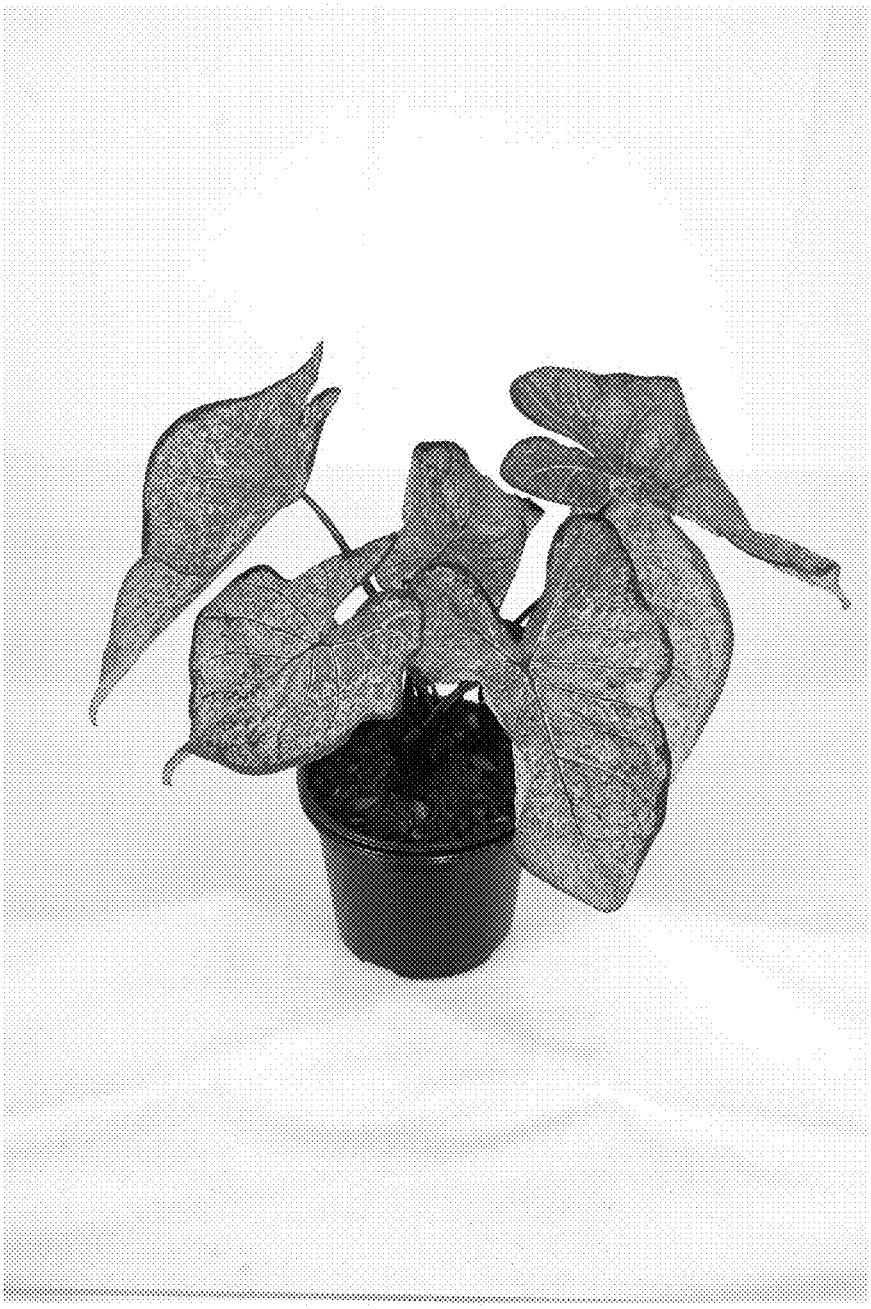

Botanical designation: *Caladium* X *hortulanum*.
Cultivar denomination: 'FCH OF13-807'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'FCH OF13-807'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Florida of *Caladium* X *hortulanum* 'Pink Beauty', not patented, as the female, or seed, parent with *Caladium* X *hortulanum* 'Red Flash', not patented, as the male, or pollen, parent. The new *Caladium* plant was discovered and selected by the Inventor as a single plant within the progeny of the stated cross-pollination in a controlled outdoor nursery environment in Avon Park, Florida in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FCH OF13-807'. These characteristics in combination distinguish 'FCH OF13-807' as a new and distinct *Caladium* plant:

1. Upright plant habit and intermediate in height; dense, leafy and bushy appearance.
2. Vigorous growth habit and rapid growth rate.
3. Large fancy-type leaves that are mostly red in color with dark green and white-colored random blotches, dark green-colored margins and dark green-colored venation.
4. Petioles that are close to black in color with yellow green and white-colored streaks and stripes.

Plants of the new *Caladium* differ primarily from plants of the female parent, 'Pink Beauty', in the following characteristics:

1. Plants of the new *Caladium* have larger leaves than plants of 'Pink Beauty'.
2. Leaves of plants of the new *Caladium* are mostly red in color with dark green and white-colored random blotches, dark green-colored margins and dark green-colored venation whereas leaves of plants of 'Pink Beauty' are olive green in color with random pink-colored blotches and bright pink to reddish purple-colored venation.
3. Petioles of plants of the new *Caladium* are close to black in color with yellow green and white-colored streaks and stripes whereas petioles of plants of 'Pink Beauty' are tannish pink in color.
4. Plants of the new *Caladium* are tolerant to full sun conditions whereas plants of 'Pink Beauty' are not tolerant to full sun conditions and are more suitable for shaded landscapes.

Plants of the new *Caladium* differ primarily from plants of the male parent, 'Red Flash', in the following characteristics:

1. Leaves of plants of the new *Caladium* are mostly red in color with dark green and white-colored random blotches, dark green-colored margins and dark green-colored venation whereas leaves of plants of 'Red Flash' have red-colored venation and interveinal areas with pink and white-colored spots and dark green-colored borders.
2. Petioles of plants of the new *Caladium* are close to black in color with yellow green and white-colored streaks and stripes whereas petioles of plants of 'Red Flash' are red and reddish brown in color.

Plants of the new *Caladium* can be compared to plants of *Caladium* X *hortulanum* 'Frieda Hemple', not patented. In side-by-side comparisons, plants of the new *Caladium* differ primarily from plants of 'Frieda Hemple' in the following characteristics:

1. Leaves of plants of the new *Caladium* are mostly red in color with dark green and white-colored random blotches, dark green-colored margins and dark green-colored venation whereas leaves of plants of 'Frieda Hemple' are medium green in color with bright red-colored centers and venation.
2. Petioles of plants of the new *Caladium* are close to black in color with yellow green and white-colored streaks and stripes whereas petioles of plants of 'Frieda Hemple' are tannish pink in color with dense brownish black-colored stippling and streaks.
3. Plants of the new *Caladium* are tolerant to full sun conditions whereas plants of 'Frieda Hemple' are not tolerant to full sun conditions and are more suitable for shaded landscapes.

Plants of the new *Caladium* can be compared to plants of *Caladium* X *hortulanum* 'Postman Joyner', not patented. In side-by-side comparisons, plants of the new *Caladium* differ primarily from plants of 'Postman Joyner' in the following characteristics:

1. Leaves of plants of the new *Caladium* are mostly red in color with dark green and white-colored random blotches, dark green-colored margins and dark green-colored venation whereas leaves of plants of 'Postman Joyner' are dark green in color with bright red-colored centers and dark red-colored venation.
2. Petioles of plants of the new *Caladium* are close to black in color with yellow green and white-colored streaks and stripes whereas petioles of plants of 'Postman Joyner' are close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'FCH OF13-807' grown in a container that has had its tuber de-eyed prior to planting.

Figure 2:
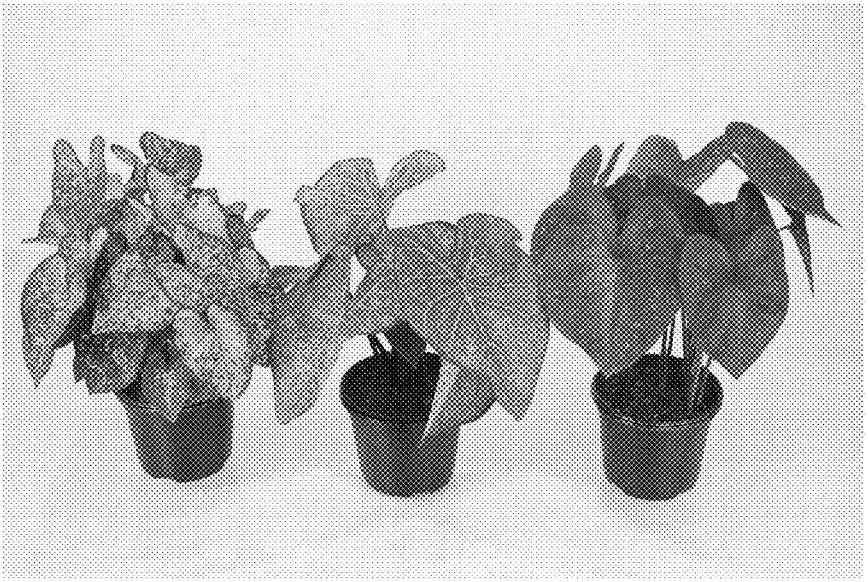

The photograph at the top of the second sheet (FIG. 2) is side perspective view of typical plants of the female parent, 'Pink Beauty' (left), 'FCH OF13-807' (center) and the male parent, 'Red Flash' (right).

Figure 3:
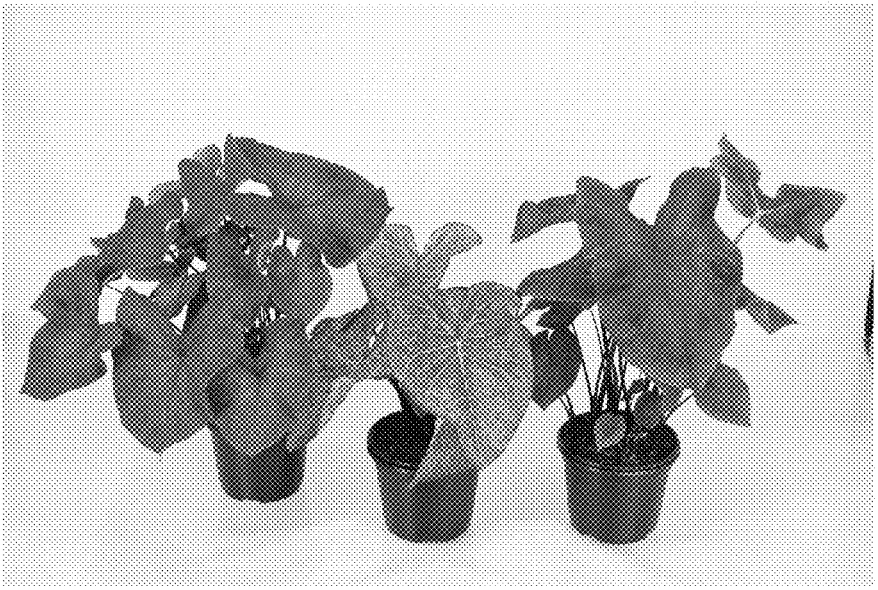

The photograph at the bottom of the second sheet (FIG. 3) is side perspective view of typical plants of 'Frieda Hemple' (left), 'FCH OF13-807' (center) and 'Postman Joyner' (right).

Figure 4:
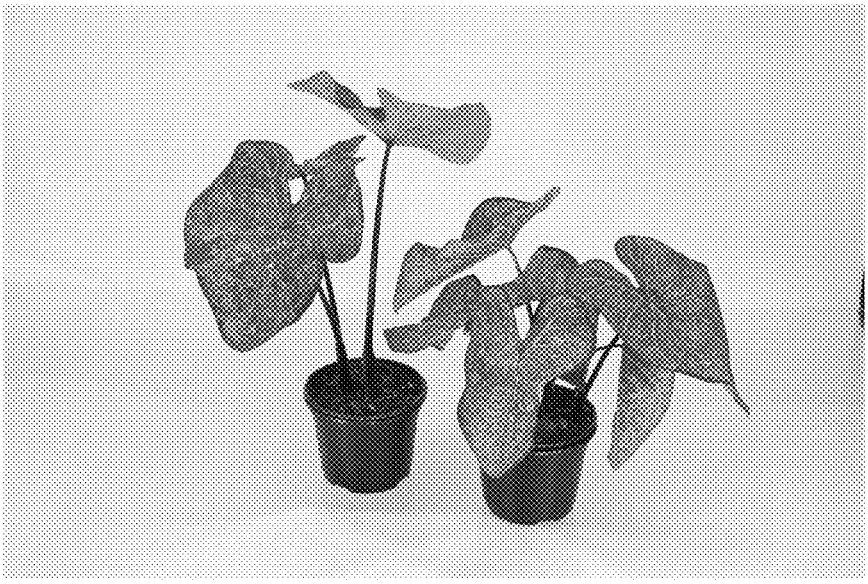

The photograph at the top of the third sheet (FIG. 4) is a comparison view of typical plants of 'FCH OF13-807' grown in containers, the plant on the left has not had its tuber de-eyed and the plant on the right has had its tuber de-eyed prior to planting.

Figure 5:
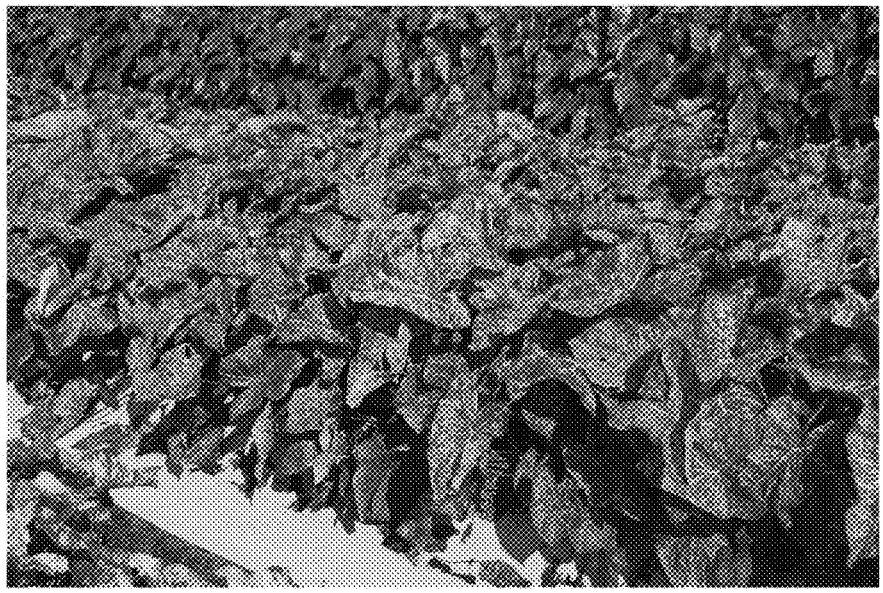

The photograph at the bottom of the third sheet (FIG. 5) is a side perspective view of typical field-grown plants of 'FCH OF13-807'.

Figure 6:
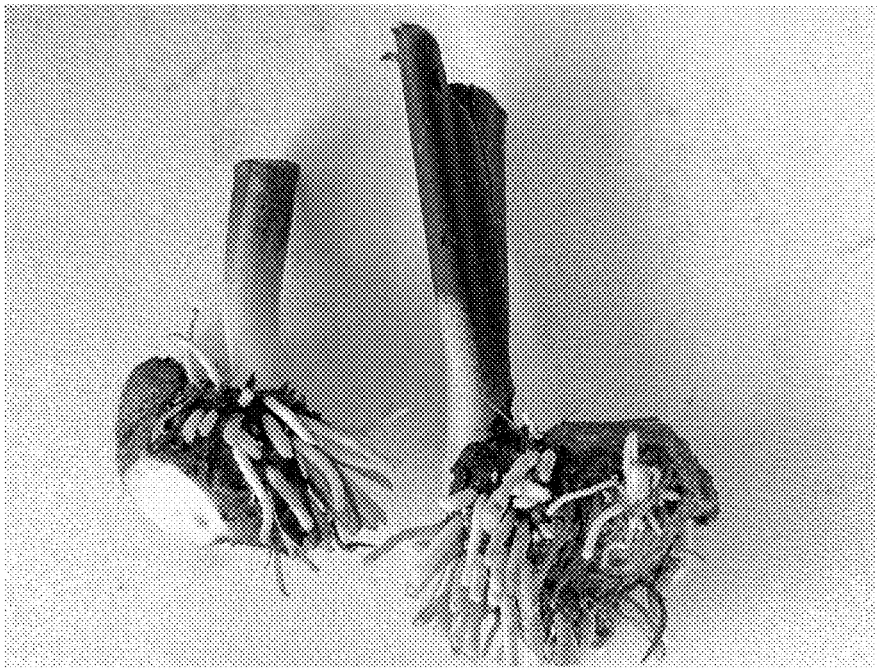

The photograph at the top of the fourth sheet (FIG. 6) is a close-up view of freshly-harvested tubers with roots of 'FCH OF13-807'.

Figure 7:
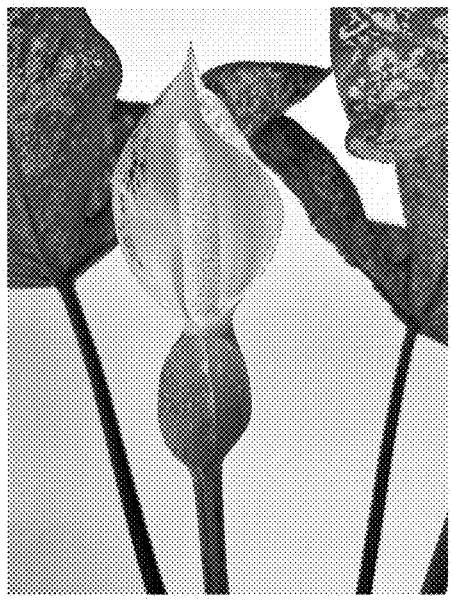

The photograph at the bottom of the fourth sheet (FIG. 7) is a close-up view of a typical inflorescence of 'FCH OF13-807'.

DETAILED BOTANICAL DESCRIPTION

The aforementioned photographs and following observations and measurements describe plants grown in 15-cm containers in a polypropylene-covered shade house (50% light reduction) in Avon Park, Florida and plants grown in ground beds under full sunlight conditions in an outdoor nursery in Zolfo Springs, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and levels were about 8,000 foot-candles. During the production of the outdoor nursery-grown plants, day temperatures ranged from about 29° C. to 35° C., night temperatures ranged from about 23° C. to 26° C. and under full sunlight conditions. Plants grown in the shade house were about eleven weeks old and plants grown in the outdoor nursery were about seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'FCH OF13-807'.

Parentage:

*Female, or seed, parent.*—*Caladium* X *hortulanum* 'Pink Beauty', not patented.

*Male, or pollen, parent.*—*Caladium* X *hortulanum* 'Red Flash', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are elliptic to ovate in shape. Height: About 3.2 cm. Diameter, largest width: About 3.7 cm to 4.5 cm. Segment height: About 1 cm. Segment diameter: About 1 cm. Axillary bud shape: Roughly triangular. Axillary bud height: About 4 mm to 5 mm. Axillary bud width: About 4 mm to 7 mm. Texture: Thick, starchy; somewhat brittle. Color: Periderm, freshly-harvested: Close to 200D and 199A. Periderm, dried: Close to 200A. Epidermis: Close to 159B and 159C. Cortical tissue: Close to 155A and 4D. Axillary buds: Close to 36B. Root description: Relatively thick, fleshy contractile roots with few lateral branches; color, close to N155D; actual color of the roots is dependent on substrate composition, water quality, fertilizer type and formulation, substrate temperature and physiological age of roots; root density, dense.

Plant description:

*Plant type*.—Herbaceous perennial; suitable as a potted plant in containers 15-cm to 25-cm and suitable as a landscape plant in shaded and full sunlight areas.

*Plant and growth habit*.—Upright plant habit; intermediate in height; overall shape, inverted triangle; dense, leafy and bushy appearance; vigorous growth habit and rapid growth rate; potted plants finish in saleable form in about seven weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 23 cm to 30 cm.

*Plant height, from soil level to top of foliar plane, shade house-grown potted plants, tubers not de-eyed*.—About 33 cm to 41 cm.

*Plant height, from soil level to top of inflorescences*.—About 39.8 cm.

*Plant diameter, shade house-grown potted plants, tubers de-eyed*.—About 35 cm to 46 cm.

*Plant diameter, shade house-grown potted plants, tubers not de-eyed*.—About 30 cm to 50 cm.

*Number of shoots per plant, shade house-grown potted plants, tubers de-eyed*.—About two to three develop per #1 tuber.

*Number of shoots per plant, shade house-grown potted plants, tubers not de-eyed*.—About one to two develop per #1 tuber.

*Cataphylls, shade house-grown potted plants*.—Length: About 6.5 cm. Width: About 1.6 cm. Shape: Lanceolate to wedge-shaped. Apex: Acute and/or cuspidate. Base: Sheathing the stem. Texture, outer and inner surfaces: Smooth, glabrous. Color, outer surface: Close to 200A and 200B with random areas, close to N170D or N155C, with stippling, close to 200A to 200B; fading to 200A with subsequent development. Color, inner surface: Close to N155C; colors and patterns on outer surface are visible on inner surface.

Leaf description:

*Arrangement and type*.—Alternate; simple; fancy-type.

*Length, shade house-grown potted plants, tubers de-eyed*.—About 15 cm to 32.7 cm.

*Width, shade house-grown potted plants, tubers de-eyed*.—About 10 cm to 17 cm; when flattened, about 13.5 cm to 22 cm.

*Shape*.—Ovate.

*Apex*.—Acute to somewhat acuminate.

*Base*.—Sagittate-peltate or cordate.

*Margin*.—Entire, with broad undulations.

*Texture and luster, upper surface*.—Somewhat rugose, glabrous; dull sheen.

*Texture and luster, lower surface*.—Somewhat rugose, glabrous; glaucous in center and around venation, dull sheen.

*Venation pattern*.—Pinnate and palmate.

*Color, shade house-grown potted plants*.—Developing and fully expanded leaves, upper surface: Interveinal areas: Mostly close to 53B, 53C and 53D, occasionally tinged with close to 185B and 185C, with random blotches, 147A surrounded with close to 155C and 155D. Margins: Close to NN137A with narrow marginal edges, close to N186C. Basal notch: Close to 187A. Leaf petiole junction: Flushed with close to N186A and 183B. Midvein and primary venation: Close to 147A and 147B surrounded with close to 155D. Secondary venation: Close to 147A surrounded with close to 192D and 155D. Developing and fully expanded leaves, lower surface: Interveinal areas: Mostly close to 55B, 55C, 51A, 59D, 56B, 56C and 54A, with random blotches, 147B and 147C surrounded with close to 155C. Margins: Close to 191A with narrow marginal edges, close to 187A. Basal notch: Close to 187B. Leaf petiole junction: Tinged with close to N200A and N186A. Midvein and largest lateral veins: Close to 194A. Smaller lateral venation: Close to 194B, 194C and N200B surrounded by close to 191A and 191B. Leaves adjacent to inflorescence, upper surface: Interveinal areas: Mostly close to 137A with blotches, close to 181A, 46A and 46B; towards the margins, a mosaic of NN155B, 146B and 181A. Margins: Narrow marginal edges, close to NN155B with spots, close to 53A and 53B. Basal notch: Close to 187A. Leaf petiole junction: Flushed with close to N186A and 203A. Midvein and lateral venation: Close to 137A. Leaves adjacent to inflorescence, lower surface: Interveinal areas: Close to 191B with random spots and blotches, close to N186C surrounded with close to 191D. Margins: Close to 191A with narrow marginal edges, close to 187A. Basal notch: Close to 191A. Midvein and largest lateral veins: Close to 194A flushed with close to 202A and N186A. Smaller lateral venation: Close to 194B and 194C.

*Petioles*.—Aspect: Initially upright and straight and leaning outwardly with development; flexible. Length, shade house-grown potted plants, tubers de-eyed: About 18 cm to 22.7 cm. Length, shade house-grown potted plants, tubers not de-eyed: About 28.2 cm to 32 cm. Diameter, distally, shade house-grown potted plants, tubers de-eyed: About 4 mm to 6 mm. Diameter, proximally, shade house-grown potted plants, tubers de-eyed: About 6 mm to 8 mm. Diameter, distally, shade house-grown potted plants, tubers not de-eyed: About 6.2 mm to 7 mm. Diameter, proximally, shade house-grown potted plants, tubers not de-eyed: About 8 mm to 10 mm. Texture and luster: Smooth, glabrous; somewhat glossy. Color, shade house-grown potted plants: When developing and developed: Close to 202A with streaks and stripes, close to 148C and 155C; just below the leaf junction, close to 202A tinged with close to 182C. Wing length, shade house-grown potted plants: About 7.3 cm to 9.7 cm. Wing diameter, shade house-grown potted plants: About 1.2 cm. Texture and luster, outer and inner surfaces: Smooth, glabrous; glossy. Wing color, shade house-grown potted plants: Outer surface: Close to 202A and N200A with marbling, close to 147C, NN155C and 56D. Inner surface: Close to N155C; colors and patterns from the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about 8.5 weeks after growth commences; inflorescences last about three days before fading; inflorescences persistent.

*Spathe*.—Length, overall: About 14.4 cm. Length, distal open portion: About 9.2 cm. Length, proximal closed portion: About 5.2 cm. Width, distal open portion: About 6 cm. Depth, distal open portion: About 2.7 cm. Width, at constriction: About 1.7 cm to 2.1 cm. Width, proximal closed portion: About 3.2 cm to 3.4 cm. Shape, open portion: Elliptic. Apex: Acute. Base: Acute. Margin: Entire. Texture and luster, front surface: Smooth, glabrous; dull sheen. Texture and luster, rear surface: Smooth, glabrous; dull sheen; proximally, glaucous and dull sheen. Color, front surface: Distal open portion: Close to N155C and 56D flushed with close to 185D, with spots and blotches, close to 187C; with subsequent development, becoming closer to 199A. Proximal closed portion: Close to 147D, at the base, faintly tinged with close to N186C; colors do not change with subsequent development. Color, rear surface: Distal open portion: Close to N155C; center, close to 145C, with spots and blotches, close to 187C and 187D; colors do not change with subsequent development. Proximal closed portion: Close to 147B; front margins, close to N155C, streaks, speckles and random areas of 157D; colors do not change with subsequent development.

*Spadix*.—Length, overall: About 10.6 cm. Length, male flower zone (including sterile flowers): About 8.6 cm. Length, sterile zone: About 2.2 cm. Length, female flower zone: About 2 cm. Diameter, male flower zone: About 1.2 cm. Diameter, sterile flower zone: About 7.5 mm. Diameter, female flower zone: About 1.1 cm. Shape: Columnar, spindle-shaped. Apex: Acute. Base: Obtuse. Aspect: Upright. Color, mature, male zone: Close to 159D. Color, mature, sterile zone: Close to 159D. Color, mature, female zone: Stigmas, close to 159D; ovaries, close to 159C. Male flowers: Quantity per spadix: About 204.Shape: Obovate. Height: About 2.4 mm. Diameter: About 3 mm. Pollen amount: Moderate. Pollen color: Close to 11D. Female flowers: Quantity per spadix: About 238. Shape: Obovate. Height: About 2.3 mm. Diameter: About 1.5 mm to 1.8 mm. Stigma color: Close to 159D. Ovary color: Close to 159C.

*Scapes*.—Length: About 25.4 cm. Diameter: About 8.3 mm to 9 mm. Strength: Sturdy; flexible. Aspect: Mostly erect, straight. Texture and luster: Smooth, glabrous; dull sheen; distally, glaucous. Color: Close to 202A, with streaks and stripes, close to 147B to 147C; distally, close to 148C, 147B and 147C flushed with close to 200A and N200A.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'FCH OF13-807' as herein illustrated and described herein.

* * * * *